(12) United States Patent
Dimitrijevs et al.

(10) Patent No.: US 8,343,127 B1
(45) Date of Patent: Jan. 1, 2013

(54) ABSORBENT ARTICLES WITH GARMENT-LIKE REFASTENABLE SEAMS

(75) Inventors: Lisa Ann Dimitrijevs, Appleton, WI (US); Amy Lynn Fletcher, Appleton, WI (US); Christopher Peter Olson, Neenah, WI (US); Kathleen Irene Ratliff, Neenah, WI (US); Shirlee Ann Weber, Neenah, WI (US); Susan Lee West, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1192 days.

(21) Appl. No.: 09/444,080

(22) Filed: Nov. 22, 1999

(51) Int. Cl.
*A61F 13/15* (2006.01)
(52) U.S. Cl. .............. 604/387; 604/386; 604/391
(58) Field of Classification Search ............ 604/385.03, 604/385.23, 385.25, 385.26, 386–387, 389, 604/390–391
See application file for complete search history.

(56) References Cited

U.S. PATENT DOCUMENTS

| | | | |
|---|---|---|---|
| 2,957,512 A | 10/1960 | Wade et al. |
| 3,039,466 A | 6/1962 | Wilson |
| 3,277,547 A | 10/1966 | Billarant |
| 3,316,139 A | 4/1967 | Alford et al. |
| 3,319,307 A | 5/1967 | Marforio |
| 3,577,607 A | 5/1971 | Ikoma et al. |
| 3,694,867 A | 10/1972 | Stumpf |
| 3,842,832 A | 10/1974 | Wideman et al. |
| 3,842,837 A | 10/1974 | Sward |
| 3,943,981 A | 3/1976 | De Brabander |
| 4,022,211 A | 5/1977 | Timmons et al. |
| 4,051,854 A | 10/1977 | Aaron |
| 4,122,552 A | 10/1978 | Tedford |
| 4,145,763 A | 3/1979 | Abrams et al. |
| 4,201,203 A | 5/1980 | Applegate |
| 4,205,679 A | 6/1980 | Repke et al. |
| 4,209,563 A | 6/1980 | Sisson |
| 4,244,368 A | 1/1981 | Caradonna |
| 4,253,461 A | 3/1981 | Strickland et al. |
| 4,259,957 A | 4/1981 | Sonenstein et al. |
| 4,338,938 A | 7/1982 | Seavitt |
| 4,402,690 A | 9/1983 | Redfern |
| 4,418,123 A | 11/1983 | Bunnelle et al. |
| 4,446,189 A | 5/1984 | Romanek |
| 4,496,360 A | 1/1985 | Joffe et al. |
| 4,516,975 A | 5/1985 | Mitchell |

(Continued)

FOREIGN PATENT DOCUMENTS

CA 2096672 11/1997

(Continued)

OTHER PUBLICATIONS

Advertisement from One Step Ahead® catalog, Late Winter 2000, cover pages and p. 26 referencing "Handy's Training Pants," and a photocopy of a package of Handy's Junior Training Pants as advertised therein.

*Primary Examiner* — Michele M Kidwell
(74) *Attorney, Agent, or Firm* — Thomas M. Gage; H. Michael Kubicki; R. Joseph Foster, III

(57) ABSTRACT

A disposable absorbent article includes a fastening system that can be repeatedly fastened, unfastened and refastened. The refastenable seams formed by the fastening system components provide a garment-like appearance.

19 Claims, 6 Drawing Sheets

U.S. PATENT DOCUMENTS

| | | |
|---|---|---|
| 4,560,381 A | 12/1985 | Southwell |
| 4,568,342 A | 2/1986 | Davis |
| 4,581,772 A | 4/1986 | Smith |
| 4,585,447 A | 4/1986 | Karami |
| 4,610,680 A | 9/1986 | LaFleur |
| 4,610,682 A | 9/1986 | Kopp |
| 4,615,695 A | 10/1986 | Cooper |
| 4,619,649 A | 10/1986 | Roberts |
| 4,623,339 A | 11/1986 | Ciraldo et al. |
| 4,650,483 A | 3/1987 | Joffe |
| 4,655,760 A | 4/1987 | Morman et al. |
| 4,657,802 A | 4/1987 | Morman |
| 4,662,875 A | 5/1987 | Hirotsu et al. |
| 4,663,220 A | 5/1987 | Wisneski et al. |
| 4,699,622 A | 10/1987 | Toussant et al. |
| 4,701,170 A | 10/1987 | Wilson et al. |
| 4,701,176 A | 10/1987 | Wilson et al. |
| 4,704,116 A | 11/1987 | Enloe |
| 4,705,710 A | 11/1987 | Matsuda |
| 4,714,096 A | 12/1987 | Guay |
| 4,718,901 A | 1/1988 | Singheimer |
| 4,720,415 A | 1/1988 | Vander Wielen et al. |
| 4,725,473 A | 2/1988 | Van Gompel et al. |
| 4,743,239 A | 5/1988 | Cole |
| 4,756,709 A | 7/1988 | Stevens |
| 4,761,318 A | 8/1988 | Ott et al. |
| 4,770,656 A | 9/1988 | Proxmire et al. |
| 4,771,483 A | 9/1988 | Hooreman et al. |
| 4,789,699 A | 12/1988 | Kieffer et al. |
| 4,834,742 A | 5/1989 | Wilson et al. |
| 4,846,825 A | 7/1989 | Enloe et al. |
| 4,847,134 A | 7/1989 | Fahrenkrug et al. |
| 4,850,988 A | 7/1989 | Aledo et al. |
| 4,850,992 A | 7/1989 | Amaral et al. |
| 4,863,785 A | 9/1989 | Berman et al. |
| 4,894,060 A | 1/1990 | Nestegard |
| 4,895,569 A | 1/1990 | Wilson et al. |
| 4,904,251 A | 2/1990 | Igaue et al. |
| 4,923,456 A | 5/1990 | Proxmire |
| 4,936,840 A | 6/1990 | Proxmire |
| 4,938,757 A | 7/1990 | Van Gompel et al. |
| 4,940,464 A | 7/1990 | Van Gompel et al. |
| 4,963,140 A | 10/1990 | Robertson et al. |
| 5,019,073 A | 5/1991 | Roessler et al. |
| 5,032,122 A | 7/1991 | Noel et al. |
| 5,046,272 A | 9/1991 | Vogt et al. |
| 5,062,839 A | 11/1991 | Anderson |
| 5,087,253 A | 2/1992 | Cooper |
| 5,104,116 A | 4/1992 | Pohjola |
| 5,114,781 A | 5/1992 | Morman |
| 5,116,662 A | 5/1992 | Morman |
| 5,151,092 A | 9/1992 | Buell et al. |
| D331,969 S | 12/1992 | Hunt |
| 5,176,671 A | 1/1993 | Roessler et al. |
| 5,185,052 A | 2/1993 | Chappell et al. |
| 5,224,405 A | 7/1993 | Pohjola |
| 5,226,992 A | 7/1993 | Morman |
| 5,242,436 A | 9/1993 | Weil et al. |
| 5,256,231 A | 10/1993 | Gorman et al. |
| 5,269,776 A | 12/1993 | Lancaster et al. |
| 5,315,716 A | 5/1994 | Baum |
| 5,318,555 A | 6/1994 | Siebers et al. |
| 5,326,612 A | 7/1994 | Goulait |
| 5,342,341 A | 8/1994 | Igaue et al. |
| 5,370,634 A | 12/1994 | Ando et al. |
| 5,380,313 A | 1/1995 | Goulait et al. |
| 5,383,872 A | 1/1995 | Roessler et al. |
| 5,385,775 A | 1/1995 | Wright |
| 5,399,219 A | 3/1995 | Roessler et al. |
| 5,401,275 A | 3/1995 | Flug et al. |
| 5,407,439 A | 4/1995 | Goulait |
| 5,413,654 A | 5/1995 | Igaue et al. |
| 5,451,219 A | 9/1995 | Suzuki et al. |
| 5,476,702 A | 12/1995 | Datta et al. |
| 5,496,298 A | 3/1996 | Kuepper et al. |
| 5,503,908 A | 4/1996 | Faass |
| 5,527,302 A | 6/1996 | Endres et al. |
| 5,531,731 A | 7/1996 | Brusky |
| 5,531,732 A | 7/1996 | Wood |
| 5,542,942 A | 8/1996 | Kline et al. |
| 5,546,608 A | 8/1996 | Russano |
| 5,547,531 A | 8/1996 | Allen et al. |
| 5,549,591 A | 8/1996 | Landvogt |
| 5,554,239 A | 9/1996 | Datta et al. |
| 5,569,233 A | 10/1996 | Goulait |
| 5,591,155 A | 1/1997 | Nishikawa et al. |
| 5,595,567 A | 1/1997 | King et al. |
| D377,980 S | 2/1997 | Slingland |
| 5,603,708 A | 2/1997 | Seth |
| 5,605,735 A | 2/1997 | Zehner et al. |
| 5,606,781 A | 3/1997 | Provost et al. |
| 5,611,791 A | 3/1997 | Gorman et al. |
| 5,615,460 A | 4/1997 | Weirich et al. |
| 5,616,394 A | 4/1997 | Gorman et al. |
| 5,618,280 A | 4/1997 | Glackin et al. |
| 5,620,432 A | 4/1997 | Goulait et al. |
| 5,624,420 A | 4/1997 | Bridges et al. |
| 5,624,427 A | 4/1997 | Bergman et al. |
| 5,624,429 A | 4/1997 | Long et al. |
| D379,226 S | 5/1997 | Kaczmarzyk et al. |
| 5,643,397 A | 7/1997 | Gorman et al. |
| 5,647,864 A | 7/1997 | Allen et al. |
| H1674 H | 8/1997 | Ames et al. |
| 5,655,843 A | 8/1997 | Conrad et al. |
| 5,669,897 A | 9/1997 | Lavon et al. |
| 5,669,900 A | 9/1997 | Bullwinkel et al. |
| 5,681,302 A | 10/1997 | Melbye et al. |
| 5,685,873 A | 11/1997 | Bruemmer |
| 5,693,038 A | 12/1997 | Suzuki et al. |
| 5,722,969 A | 3/1998 | Ito et al. |
| 5,735,840 A | 4/1998 | Kline et al. |
| 5,749,866 A | 5/1998 | Roe et al. |
| 5,759,181 A | 6/1998 | Sayama et al. |
| 5,766,389 A | 6/1998 | Brandon et al. |
| 5,779,831 A | 7/1998 | Schmitz |
| 5,782,819 A | 7/1998 | Tanzer et al. |
| 5,785,699 A | 7/1998 | Schmitz |
| 5,795,350 A | 8/1998 | Schmitz |
| H1750 H | 9/1998 | Dobrin |
| 5,814,178 A | 9/1998 | Jacobs |
| 5,830,206 A | 11/1998 | Larsson |
| 5,830,298 A | 11/1998 | Jackson |
| 5,843,068 A | 12/1998 | Allen et al. |
| 5,846,262 A | 12/1998 | Sayama et al. |
| 5,851,205 A | 12/1998 | Hisada et al. |
| 5,853,405 A | 12/1998 | Suprise |
| 5,855,574 A | 1/1999 | Kling et al. |
| 5,858,012 A | 1/1999 | Yamaki et al. |
| 5,876,394 A | 3/1999 | Rosch et al. |
| 5,879,500 A | 3/1999 | Herrin et al. |
| 5,888,607 A | 3/1999 | Seth et al. |
| 5,891,122 A | 4/1999 | Coates |
| 5,891,547 A | 4/1999 | Lawless |
| 5,897,545 A * | 4/1999 | Kline et al. ............ 604/386 |
| 5,897,546 A | 4/1999 | Kido et al. |
| 5,897,547 A | 4/1999 | Schmitz |
| 5,899,895 A | 5/1999 | Robles et al. |
| 5,906,008 A | 5/1999 | Heki et al. |
| 5,911,713 A | 6/1999 | Yamada et al. |
| 5,921,977 A | 7/1999 | Schmitz |
| 5,925,027 A | 7/1999 | Schmitz |
| 5,926,926 A | 7/1999 | Kato |
| 5,928,212 A | 7/1999 | Kline et al. |
| 5,957,908 A | 9/1999 | Kline et al. |
| 5,967,665 A | 10/1999 | MacDonald et al. |
| 5,968,031 A | 10/1999 | Schmitz |
| 5,997,521 A | 12/1999 | Robles et al. |
| 5,997,981 A | 12/1999 | McCormack et al. |
| 6,009,558 A | 1/2000 | Rosch et al. |
| 6,022,430 A | 2/2000 | Blenke et al. |
| 6,027,485 A | 2/2000 | Matsushita et al. |
| 6,030,373 A | 2/2000 | VanGompel et al. |
| D421,802 S | 3/2000 | Van Gompel et al. |
| D422,077 S | 3/2000 | Suprise et al. |
| D422,078 S | 3/2000 | Vukos et al. |
| 6,063,466 A | 5/2000 | Tuschy et al. |
| 6,086,571 A * | 7/2000 | Guevara et al. ............ 604/385.2 |

| | | | | | | |
|---|---|---|---|---|---|---|
| 6,099,516 | A | 8/2000 | Pozniak et al. | EP | 0 951 266 B1 | 3/2002 |
| 6,113,717 | A | 9/2000 | Vogt et al. | EP | 0 994 689 B1 | 9/2002 |
| 6,115,847 | A | 9/2000 | Rosch et al. | FR | 1375254 | 9/1963 |
| 6,146,738 | A | 11/2000 | Tsuji et al. | GB | 1 520 740 | 8/1978 |
| D437,932 | S | 2/2001 | Ruman et al. | GB | 2 088 483 A | 6/1982 |
| D437,933 | S | 2/2001 | Fletcher et al. | GB | 2 267 024 A | 11/1993 |
| 6,192,521 | B1 | 2/2001 | Alberts et al. | GB | 2 303 045 A | 2/1997 |
| D438,614 | S | 3/2001 | Ratliff et al. | GB | 2 315 402 A | 2/1998 |
| D439,662 | S | 3/2001 | Ratliff et al. | JP | 5-84322 U | 11/1993 |
| 6,210,388 | B1 | 4/2001 | Widlund et al. | JP | 6-30962 A | 2/1994 |
| 6,213,991 | B1 * | 4/2001 | Kliing et al. ............ 604/385.01 | JP | 6-55623 U | 8/1994 |
| 6,230,374 | B1 | 5/2001 | Widlund | JP | 6-285113 A | 10/1994 |
| 6,264,643 | B1 | 7/2001 | Toyoda | JP | 7-116191 A | 5/1995 |
| 6,287,287 | B1 | 9/2001 | Elsberg | JP | 9-66071 A | 3/1997 |
| 6,302,871 | B1 | 10/2001 | Nakao et al. | JP | 9-187477 A | 7/1997 |
| 6,328,725 | B2 | 12/2001 | Fernfors | JP | 11-99178 A | 4/1999 |
| 6,329,016 | B1 | 12/2001 | Shepard et al. | WO | WO 93/17648 A1 | 9/1993 |
| 6,332,250 | B1 | 12/2001 | Igaue et al. | WO | WO 95/02383 A1 | 1/1995 |
| 6,352,528 | B1 | 3/2002 | Weber et al. | WO | WO 95/18589 A1 | 7/1995 |
| 6,447,497 | B1 | 9/2002 | Olson | WO | WO 95/27460 A1 | 10/1995 |
| 6,454,751 | B1 | 9/2002 | Olson | WO | WO 95/27461 A1 | 10/1995 |
| 6,461,344 | B1 | 10/2002 | Widlund et al. | WO | WO 95/27462 A1 | 10/1995 |
| 6,645,190 | B1 | 11/2003 | Olson et al. | WO | WO 95/27463 A1 | 10/1995 |
| 6,761,711 | B1 | 7/2004 | Fletcher et al. | WO | WO 95/29657 A1 | 11/1995 |
| 6,764,475 | B1 | 7/2004 | Olson | WO | WO 96/03950 A1 | 2/1996 |
| 6,849,067 | B2 | 2/2005 | Fletcher et al. | WO | WO 96/19960 A1 | 7/1996 |
| 2002/0095131 | A1 | 7/2002 | Olson | WO | WO 96/41604 A1 | 12/1996 |
| 2002/0099353 | A1 | 7/2002 | Olson | WO | WO 97/04729 A1 | 2/1997 |
| 2004/0092903 | A1 | 5/2004 | Olson et al. | WO | WO 97/23180 A1 | 7/1997 |
| | | | | WO | WO 97/36566 A1 | 10/1997 |
| | | FOREIGN PATENT DOCUMENTS | | WO | WO 97/46197 A1 | 12/1997 |
| DE | | 35 33 881 A1 | 4/1986 | WO | WO 97/48359 A1 | 12/1997 |
| DE | | 196 54 052 C1 | 12/1997 | WO | 98/18421 * | 5/1998 |
| DE | | 197 27 916 A1 | 6/1998 | WO | WO 98/18421 A1 | 5/1998 |
| EP | | 0 217 032 B1 | 2/1992 | WO | WO 98/18422 A1 | 5/1998 |
| EP | | 0 520 087 A1 | 12/1992 | WO | WO 98/51252 A1 | 11/1998 |
| EP | | 0 526 868 A2 | 2/1993 | WO | WO 99/53881 A1 | 10/1999 |
| EP | | 0 528 282 A2 | 2/1993 | WO | WO 99/65441 A1 | 12/1999 |
| EP | | 0 321 232 B1 | 5/1993 | WO | WO 00/15069 A1 | 3/2000 |
| EP | | 0 320 991 B1 | 5/1994 | WO | WO 00/19950 A1 | 4/2000 |
| EP | | 0 622 063 A2 | 11/1994 | WO | WO 00/19951 A1 | 4/2000 |
| EP | | 0 476 992 B1 | 7/1995 | WO | WO 00/20206 A1 | 4/2000 |
| EP | | 0 487 921 B1 | 9/1995 | WO | WO 00/20207 A1 | 4/2000 |
| EP | | 0 433 951 B1 | 8/1996 | WO | WO 00/23025 A1 | 4/2000 |
| EP | | 0 696 911 B1 | 1/1997 | WO | WO 00/27236 A1 | 5/2000 |
| EP | | 0 756 855 A1 | 2/1997 | WO | WO 00/27328 A1 | 5/2000 |
| EP | | 0 570 980 B1 | 7/1997 | WO | WO 00/27329 A1 | 5/2000 |
| EP | | 0 812 584 A2 | 12/1997 | WO | WO 00/30581 A1 | 6/2000 |
| EP | | 0 878 180 A2 | 11/1998 | WO | WO 00/30584 A1 | 6/2000 |
| EP | | 0 757 550 B1 | 12/1998 | WO | WO 00/35396 A1 | 6/2000 |
| EP | | 0 945 110 A2 | 9/1999 | WO | WO 00/35397 A1 | 6/2000 |
| EP | | 0 641 552 B1 | 12/1999 | WO | WO 00/35398 A1 | 6/2000 |
| EP | | 0 755 239 B1 | 12/1999 | WO | WO 00/35399 A1 | 6/2000 |
| EP | | 0 800 379 B1 | 12/1999 | WO | WO 00/37009 A2 | 6/2000 |
| EP | | 0 719 534 B1 | 4/2000 | WO | WO 00/37016 A1 | 6/2000 |
| EP | | 0 721 769 B1 | 5/2000 | WO | WO 00/74621 A1 | 12/2000 |
| EP | | 0 721 770 B1 | 5/2000 | WO | WO 01/88245 A2 | 11/2001 |
| EP | | 0 547 497 B2 | 7/2000 | | | |
| EP | | 0 765 148 B1 | 11/2000 | | * cited by examiner | |

ABSORBENT ARTICLES WITH GARMENT-LIKE REFASTENABLE SEAMS

BACKGROUND OF THE INVENTION

The present invention relates to absorbent articles which are adapted to contain body exudates. More particularly, the invention pertains to pant-like disposable absorbent articles having garment-like refastenable seams, and methods of making such disposable absorbent articles.

Current disposable absorbent training pants for children going through the potty training stage have proved to be a particularly desirable and useful product. Such training pants generally include an absorbent chassis including a liquid impervious outer cover, a liquid pervious bodyside liner and an absorbent structure. The training pants further include stretchable side panels that are permanently bonded to opposite side edges of the absorbent chassis. The chassis and side panels thereby form a unitary waist opening and two leg openings. The fit of the pants may be further enhanced by gathering means along the waist and leg openings.

The components of traditional training pants are permanently seamed together to provide a pant product. These products are particularly appealing to caregivers and are useful in the toilet training process because the pant has a very garment-like look. Children identify diaper products with babies, and most children do not like being identified with or as babies. Consequently, these children do not want to wear baby diapers, and instead prefer to wear training pants that look like adult underwear. Thus, the switch from a traditional diaper to a more garment-like or underwear-like training pant can be an important step in the toilet training process.

One drawback with current training pants, however, is that the manner of applying them is limited to being pulled on like a pant. Applying the product like a pant is advantageous in many instances, and is particularly suited for active, walking children. Even for the same child, however, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied either like a diaper or a pant permits the interior of the product to be easily checked without having to pull the product downward.

Thus, it would be desirable to have a disposable absorbent article that provides the garment-like or underwear-like look of a traditional training pant yet affords the option of being applied either like a diaper or like a pant.

SUMMARY OF THE INVENTION

In response to the above-referenced unfulfilled need in the art, a new pant-like disposable absorbent article having garment-like refastenable seams and a method of making such a disposable absorbent article have been discovered. The absorbent article includes a fastening system that can be repeatedly fastened, unfastened and refastened. The refastenable seams formed by the fastening system components provide a garment-like appearance.

In one embodiment, the present invention pertains to an absorbent article including an absorbent chassis that defines a longitudinal axis, a transverse axis, a first or front waist edge and a second or back waist edge which are parallel to the transverse axis, and opposite side edges that extend between the front and back waist edges. The absorbent chassis also defines a first or front waist region contiguous with the front waist edge, a second or back waist region contiguous with the back waist edge, and a crotch region which extends between and interconnects the front and back waist regions. The absorbent chassis includes a rectangular composite structure having opposite linear side edges parallel to the longitudinal axis and opposite linear end edges parallel to the transverse axis. The composite structure includes a bodyside liner, an outer cover bonded to the bodyside liner, and an absorbent assembly disposed between the bodyside liner and the outer cover. A pair of elastomeric side panels is bonded to the composite structure in the back waist region, with each side panel being elastomeric in a direction parallel to the transverse axis. The absorbent article also includes a fastening system for releasably securing the absorbent article in a pant-like configuration. The fastening system includes first and second fastening components adapted to releasably engage first and second mating fastening components. The fastening components are disposed on the elastomeric side panels and having a length dimension, a width dimension, and a length-to-width ratio of about 2 or greater. The mating fastening components are disposed in the front waist region and positioned along the opposite side edges abutting the front waist edge.

The fastening components and the mating fastening components form refastenable seams for securing the first and second waist regions together. The refastenable seams allow the product to be either pulled on like a pant or applied like a diaper. If the training pant becomes soiled during use, the fastening components can be disengaged from the mating fastening components to easily remove the training pant from the waist of the wearer with reduced risk of undesirably soiling the clothes or legs of the wearer. Further, the fastening components can also be easily disengaged from the mating fastening components to inspect the training pant for possible soiling. Thus, the training pant is configured to be pulled on or off over the hips of the wearer such as conventional training pants and can be readily applied or removed by disengaging the fastening components similar to conventional diapers. Moreover, the first and second fastening components can be repositioned if necessary after the training pant has been pulled on over the legs and hips of the wearer.

This embodiment of the invention also provides an absorbent article that is extremely compatible with high-speed manufacturing processes. The composite structure can be formed as a rectangular shape and the elastomeric side panels joined to the composite structure with their waist end edges forming part of the back waist edge of the absorbent article.

The design of the absorbent chassis and the fastening components provides the absorbent article with a garment-like appearance. The refastenable seams in particular can be integrated within the absorbent chassis so that they are flush with the overall exterior product shape. The garment-like seams are thus less likely to disengage inadvertently. The refastenable seams may also be made less noticeable and as a result may be made harder for children to open without guidance. Additionally, the fastening system components can be incorporated into the absorbent article without interfering with existing outer cover graphics, which have become an important interactive toilet training feature in current training pants.

The garment-like fit of the absorbent article can be improved by the incorporation of leg elastic members that are longitudinally aligned along each side edge of the absorbent chassis. In particular embodiments, the leg elastic members are also axially aligned with the mating fastening components. This not only creates an absorbent article that is suited for high-speed manufacture, but also advantageously positions the mating fastening components at the front of the wearer's body. Desirably, the front terminal points of the leg elastic members may be located adjacent inner end edges of the respective mating fastening components, for example within about 2 centimeters of the mating fastening components, particularly within about 1 centimeter of the mating fastening components, and more particularly abutting or slightly overlapping the mating fastening components, and the back terminal points may be located adjacent longitudinally innermost parts of the side panels, for example within about 2 centimeters of the longitudinally innermost parts of the side panels, particularly within about 1 centimeter of the longitudinally innermost parts of the side panels, and more particularly at the same location or slightly extending beyond the longitudinally innermost parts of the side panels.

Hence, in another embodiment, the present invention pertains to an absorbent article including an absorbent chassis comprising a bodyside liner, an outer cover bonded to the bodyside liner, and an absorbent assembly disposed between the bodyside liner and the outer cover. The absorbent chassis defines a longitudinal axis, a transverse axis, an overall length dimension, front and back waist edges parallel to the transverse axis, opposite side edges extending between the front and back waist edges, a front waist region contiguous with the front waist edge, a back waist region contiguous with the back waist edge, and a crotch region which extends between and interconnects the front and back waist regions. The side edges in the front waist region and crotch region are aligned with one another parallel to the longitudinal axis. First and second side panels extend transversely outward from the absorbent assembly in the back waist region. The side panels have opposite waist end and leg end edges and an average length dimension that is about 20 percent or greater of the overall length dimension. Leg elastic members are longitudinally aligned along each side edge. A fastening system of the absorbent article releasably secures the absorbent article in a pant-like configuration. The fastening system includes first and second fastening components that are adapted to releasably engage first and second mating fastening components. Each of the fastening components and the mating fastening components have a length dimension aligned generally parallel to the longitudinal axis, a width dimension, and a length-to-width ratio of about 5 or greater. The fastening components are disposed on the side panels, and cover about 80 to 100 percent of the distance between the opposite edges of the side panels. The mating fastening components are disposed in the front waist region along the opposite side edges abutting the front waist edge. The leg elastic members are axially aligned with the mating fastening components.

The positioning of the mating fastening components can also be enhanced by positioning inner side edges of the mating fastening components transversely outward from and adjacent to the side edges of the primary absorbent structure of the absorbent article. In doing so, the fastening components and the mating fastening components tend to form a butt joint that minimizes overlap of the front and back waist regions and further enhances the garment-like appearance of the absorbent article. This positioning of the fastening components also causes the refastenable seams to become more flush with the primary absorbent structure of the absorbent article.

In another embodiment, the present invention pertains to an absorbent article including a generally inelastic absorbent chassis comprising a bodyside liner, an outer cover bonded to the bodyside liner, and an absorbent assembly disposed between the bodyside liner and the outer cover. The absorbent chassis defines a longitudinal axis, a transverse axis, front and back waist edges parallel to the transverse axis, opposite side edges extending between the front and back waist edges, a front waist region contiguous with the front waist edge, a back waist region contiguous with the back waist edge, and a crotch region which extends between and interconnects the front and back waist regions. First and second elastomeric side panels extend transversely outward from the absorbent assembly in the back waist region. The absorbent article also includes a fastening system for releasably securing the absorbent article in a pant-like configuration. The fastening system includes first and second fastening components adapted to releasably engage first and second mating fastening components. The fastening components are disposed on the elastomeric side panels and having a length dimension, a width dimension, and a length-to-width ratio of about 2 or greater. The mating fastening components are disposed on the generally inelastic absorbent chassis in the front waist region and positioned along the opposite side edges abutting the front waist edge.

This embodiment of the invention provides an absorbent article with efficient utilization of elastomeric materials to obtain proper fit on the wearer. The absorbent article can be formed with a generally inelastic absorbent chassis, which as that term is used herein, refers to the combined structure of a bodyside liner, an outer cover and an absorbent assembly where neither the bodyside liner nor the outer cover is formed with a unitary elastomeric material. In particular, leg elastic members and waist elastic members may be operatively joined to the combined structure, but the bodyside liner and outer cover materials themselves are not elastomeric. The inelastic absorbent chassis desirably concentrates the elastic forces over the hips and around the back side of the wearer. Concentration of elastic forces in these areas is more efficient for holding the product up on the wearer than is concentration of elastic forces across the front waist region. The inelastic absorbent chassis also avoids the difficulties in mounting a non-stretchable absorbent in an elastic chassis. Inelastic liners and outer covers can be more suitable for containing the absorbent structure, in that they help prevent uncomfortable bunching and migration of absorbent material through the liner and onto the skin.

In another embodiment, the present invention pertains to an absorbent article including a generally inelastic absorbent chassis and a fastening system for releasably attaching a front waist region of the absorbent chassis to a back waist region of the absorbent chassis to define a refastenable pant. The refastenable pant has a waist opening and a pair of leg openings and includes: a pair of refastenable seams extending from the waist opening to each leg opening; a pair of elastomeric side panels extending from the waist opening to each leg opening; an elastomeric front waistband disposed in the front waist region and positioned between the pair of refastenable seams; an elastomeric back waistband disposed in the back waist region and positioned between the pair of elastomeric side panels; and a pair of elastomeric leg members which partially encircle each leg opening, where each elastomeric leg member extends from adjacent a refastenable seam in the front waist region to adjacent an elastomeric side panel in the back waist region.

This embodiment of the invention provides an absorbent article that provides fit and comfort comparable to conventional training pants, yet provides the added benefits of refastenability. The elastomeric side panels generally span the hips of the wearer and provide elasticity from the waist opening to each leg opening. The absorbent article fits closely about the body of the wearer due to the combination of the elastomeric side panels, the elastomeric front waistband, the elastomeric back waistband, and the elastomeric leg members, without the need for an elastomeric absorbent chassis. The absorbent article is securely held in place with a garment-like seam due to the refastenable seams extending from the waist opening to each leg opening.

The refastenable seams are formed when the first and second fastening components are engaged with the first and second mating fastening components. The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20-34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension is aligned generally parallel to the longitudinal axis of the absorbent article and the width dimension is aligned generally parallel to the transverse axis of the absorbent article. The term "generally parallel" as used herein refers to an angle within about 35 degrees or less of the referenced axis, and more particularly within about 20 degrees or less of the referenced axis.

The fastening components may comprise any refastenable fasteners suitable for absorbent articles, such as mechanical fastening elements or adhesive fastening elements. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop-fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

As disclosed in copending U.S. Patent Application Ser. No. 60/112,709, filed on Dec. 18, 1998 by C. P. Olson et al. and titled "Absorbent Articles Having Differential Strength Refastenable Seam," the refastenable seam can include one or more main refastenable attachment zones and one or more enhanced refastenable attachment zones. The main and enhanced refastenable attachment zones may be constructed to provide differential levels of securement, and particularly augmented levels of securement at locations which are subject to greater levels of separation forces.

As disclosed in copending U.S. Patent Application Ser. No. 60/112,775, filed on Dec. 18, 1998 by C. P. Olson and titled "Absorbent Articles Having Hinged Fasteners," the refastenable seam may comprise individual fastening materials with narrow spacings therebetween. The narrow spacings provide a desirable hinge to improve fit and securement of the fastening components.

The disclosed absorbent articles are adapted to be worn adjacent to the body of a wearer to absorb and contain various exudates discharged from the body. The absorbent articles are desirably pre-fastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system may be used with a wide variety of absorbent products, including training pants, diapers, incontinence garments, or other garments using mechanical or adhesive fasteners.

The present invention also pertains to a method of making an absorbent article. In one embodiment, a method of making an absorbent article comprises: providing an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, and a crotch region which extends between and interconnects the front and back waist regions, the absorbent chassis comprising a rectangular composite structure having linear side edges parallel to the longitudinal axis and opposite linear end edges parallel to the transverse axis, the composite structure comprising a bodyside liner, an outer cover bonded to the bodyside liner, and an absorbent assembly disposed between the bodyside liner and the outer cover; bonding a pair of elastomeric side panels to the rectangular composite structure in the back waist region, the side panels being elastomeric in a direction parallel to the transverse axis; bonding first and second fastening components to the elastomeric side panels, each of the fastening components having a length dimension, a width dimension, and a length-to-width ratio of about 2 or greater; and bonding first and second mating fastening components to the absorbent chassis in the front waist region along the opposite side edges abutting the front waist edge, the fastening components adapted to releasably engage the mating fastening components.

A more detailed description of the construction and design of one form of training pant can be found in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, is at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven web" means a web of material which is formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two Elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably connected," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a nonsoftened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article and its method of manufacture. Examples of such suitable articles include diapers, training pants, feminine hygiene products, incontinence products, other personal care or health care garments, or the like. For ease of explanation, the description hereafter will be in terms of a child's training pant.

Figure 1:
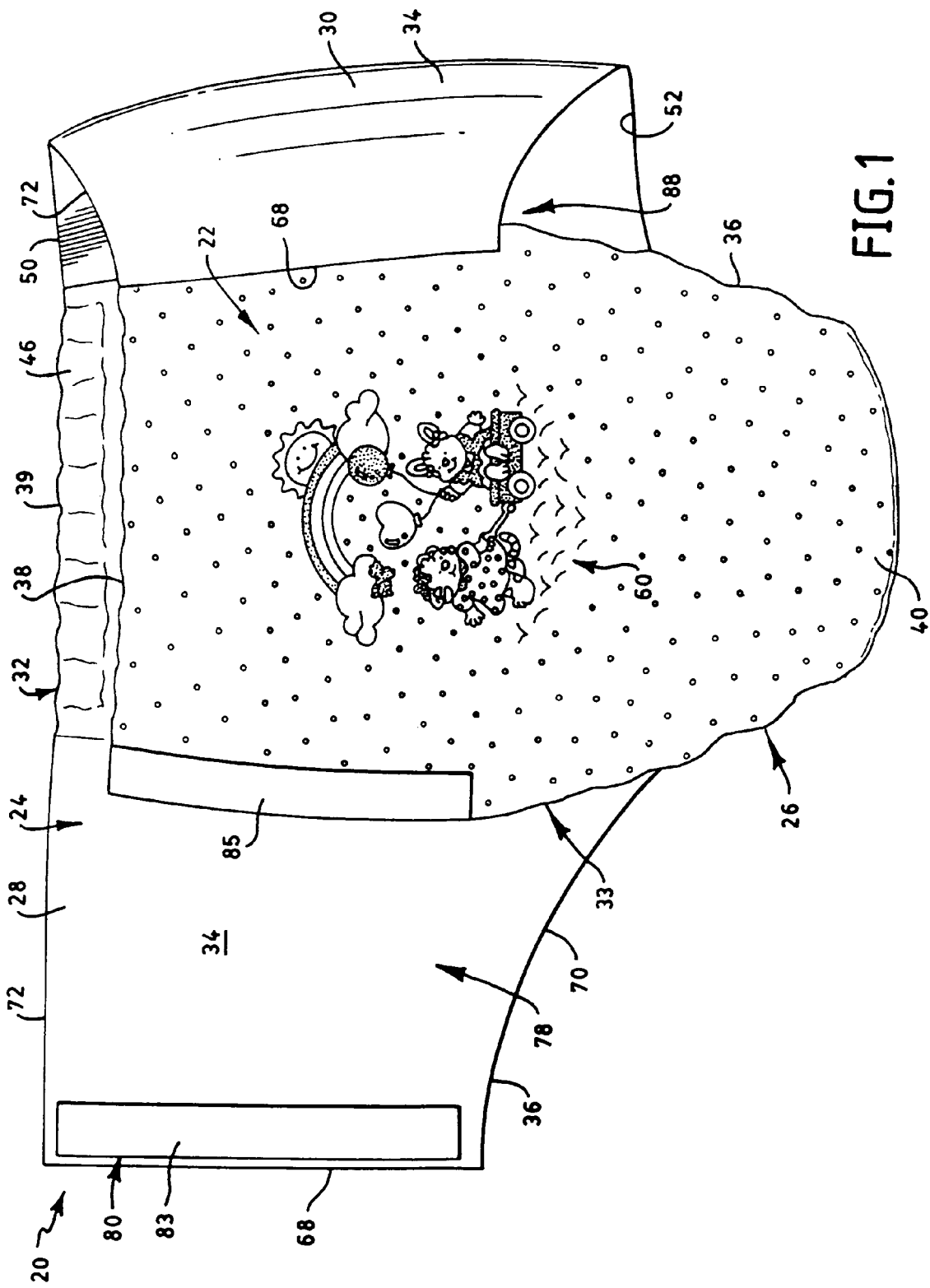
FIG. 1 illustrates a front perspective view of one type of disposable absorbent article incorporating the principles of the present invention, where the fastening system is shown engaged on one side of the absorbent article and disengaged on the other side of the absorbent article.

With reference to FIG. 1, a disposable absorbent article, such as a training pant 20, is illustrated in a partially fastened condition. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 2:
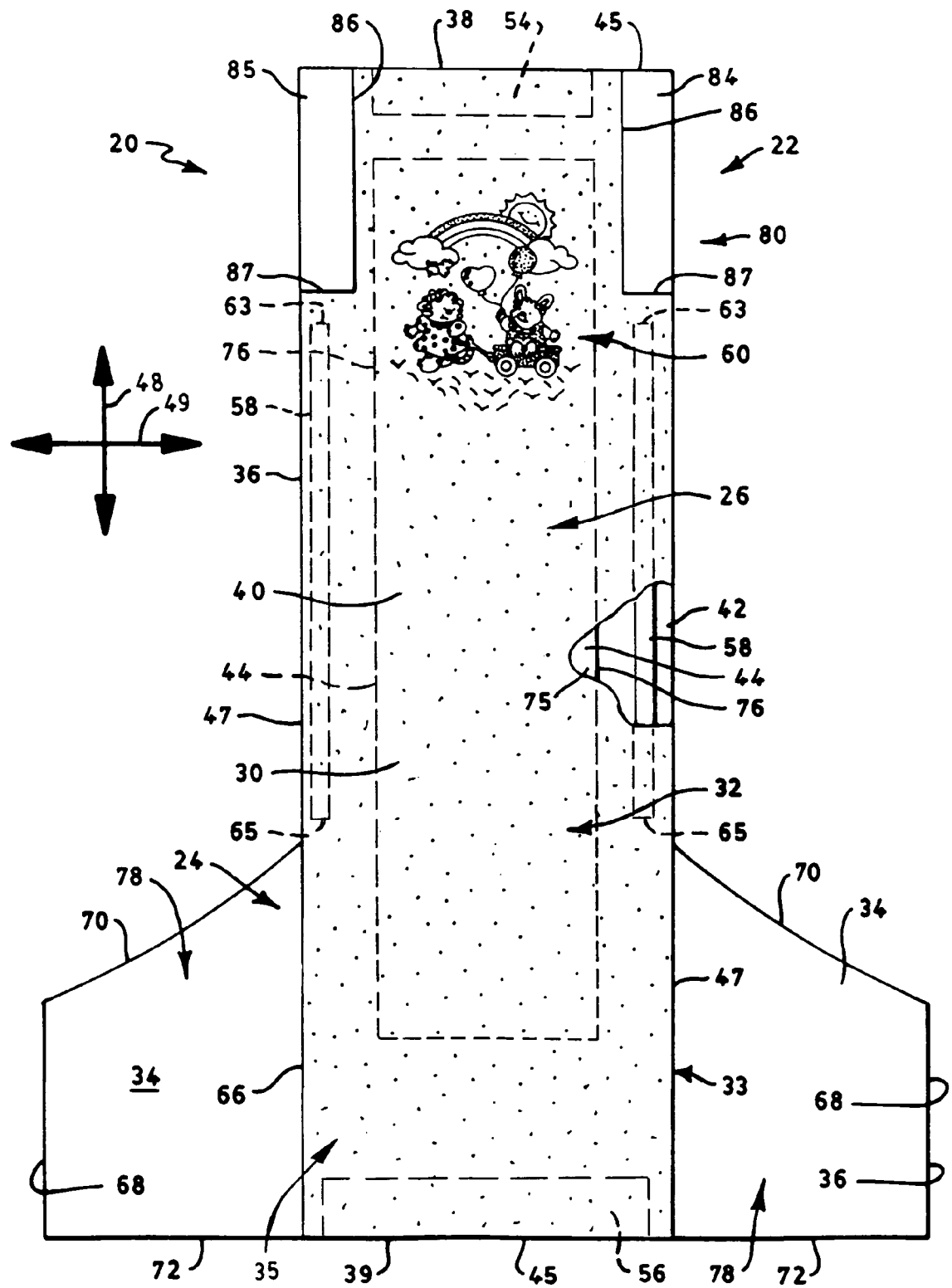
FIG. 2 illustrates a plan view of the disposable absorbent article shown in FIG. 1 in an unfastened, stretched and laid flat condition, and showing the surface of the article that faces away from the wearer, with portions cut away to show the underlying features.
Figure 3:
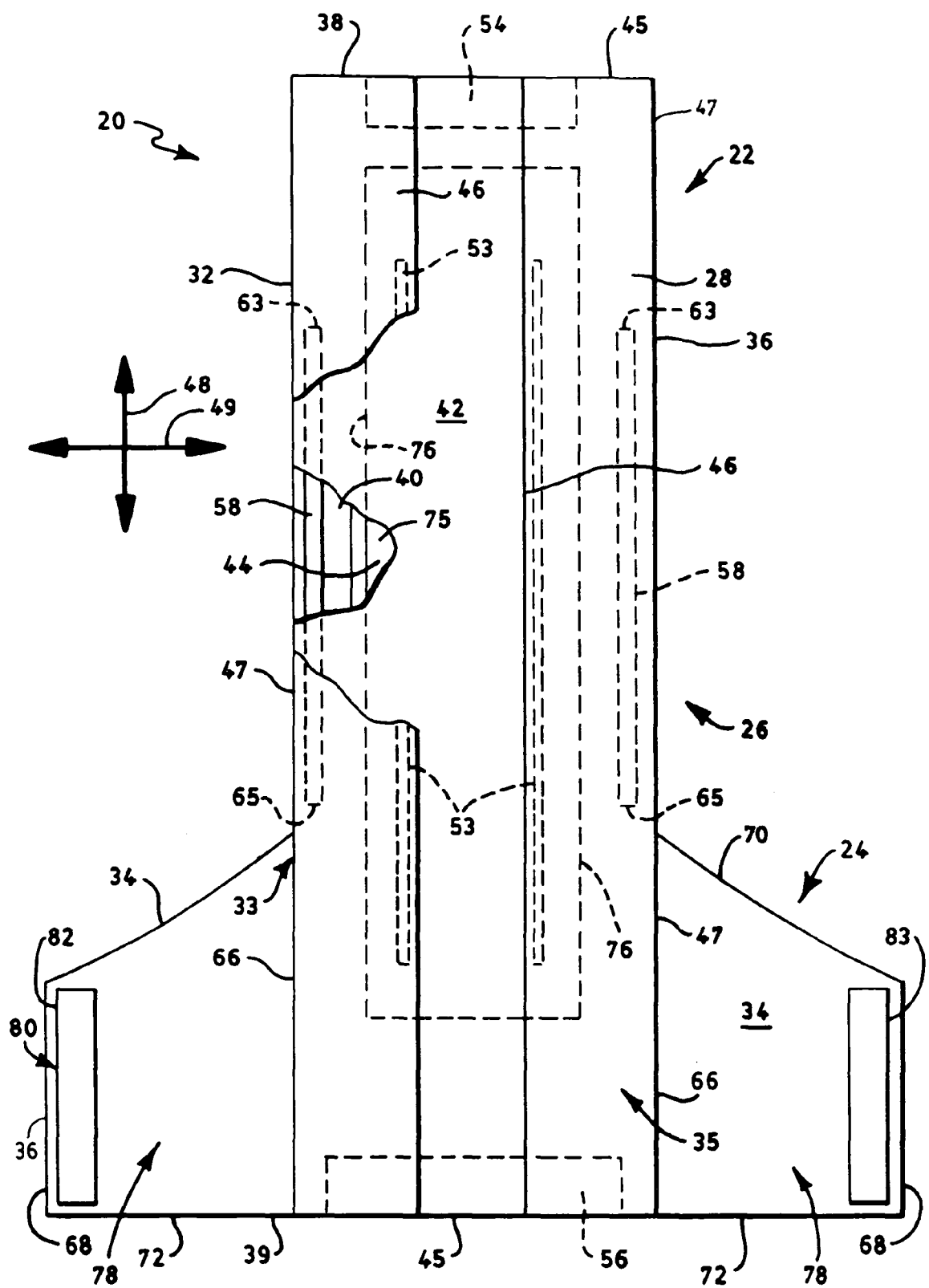
FIG. 3 illustrates a plan view similar to FIG. 2, but showing the surface of the article that faces the wearer when the article is worn, and with portions cut away to show the underlying features.

The illustrated absorbent chassis 32 comprises a rectangular composite structure 33 and a pair of transversely opposed side panels 34. The composite structure 33 and side panels 34 may be integrally formed or comprise two or more separate elements, as shown in FIG. 1. The illustrated composite structure 33 comprises an outer cover 40, a bodyside liner 42 which is connected to the outer cover in a superposed relation, an absorbent assembly 44 (FIGS. 2 and 3) which is located between the outer cover and the bodyside liner, and a pair of containment flaps 46 (FIGS. 1 and 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The back waist region 24 of the absorbent chassis 32 includes the transversely opposed side panels 34 and a center panel 35 (FIGS. 2 and 3) positioned between and connecting the side panels.

The waist edges 38 and 39 of the absorbent chassis 32 and the side panels 34 are configured to encircle the waist of the wearer when worn and provide the waist opening 50 which defines a waist perimeter dimension. Portions of the transversely opposed side edges 36 of the absorbent chassis 32 and the side panels 34 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges.

The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members.

The flap elastic members 53, the waist elastics 54 and 56, and the leg elastics 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material that is substantially liquid impermeable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like is texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 1.0 mil polyethylene film commercially available from Edison Plastics Company of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the outer cover graphic 60 includes a rainbow, sun, clouds, wagon and balloon. Again, any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can comprise elastomeric materials, it is particularly desirable in some embodiments described herein for the outer cover and bodyside liner to comprise materials that are generally not elastomeric.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, 0-47805 Krefeld, Federal Republic of Germany. Typically, a superabsorbent material is capable of absorbing at least about 15 times its weight in Water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation located in Portsmouth, Va. U.S.A.

For purposes of the present invention, the absorbent assembly 44 is considered to have an absorbent batt 75 that represents the primary absorbent structure of the absorbent assembly. The absorbent batt 75 includes opposite side edges 76 that are generally longitudinally oriented within the absorbent chassis 32 (FIGS. 2 and 3).

As noted previously, the illustrated training pant 20 has a side panel 34 disposed on each side of the absorbent chassis 32. The pair of transversely opposed side panels 34 are permanently bonded to the composite structure 33 of the absorbent chassis 32 in at least one of the waist regions 22 and 24 and releasably attached to the absorbent chassis in the opposite waist region. For example, as shown best in FIGS. 2 and 3, the side panels 34 are permanently bonded to and extend transversely beyond the side edges 47 of the composite structure 33 in the back waist region 24 along an attachment line 66.

The illustrated side panels 34 define a distal edge 68 that is spaced from the attachment line 66, a leg end edge 70, and a waist end edge 72. The leg end edge 70 and waist end edge 72 extend from the side edges 47 of the composite structure 33 to the distal edges 68. The leg end edges 70 of the side panels 34 form part of the side edges 36 of the absorbent chassis 32 and are desirably although not necessarily angled relative to the transverse axis 49 to provide greater coverage toward the back of the pant as compared to the front of the pant. The waist end edges 72 are desirably parallel to the transverse axis 49 and form part of the back waist edge 39 of the absorbent chassis 32. Further, the waist end edges 72 are desirably substantially aligned with the linear end edges 45 of the composite structure 33, and particularly longitudinally offset by about 1 centimeter or less.

In particular embodiments for improved fit and appearance, the side panels 34 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 desirably have an average length dimension of about 10 centimeters or greater, such as about 15 centimeters. As illustrated the side panels 34 extend from the waist opening 50 to one of the leg openings 52 and have a continually decreasing length dimension moving from the attachment line 66 to the distal edge 68.

The side panels 34 are permanently bonded to the composite structure 33 along the attachment line 66 using attachment means known to those skilled in the art such as adhesive, thermal or ultrasonic bonding. In such a configuration, each of the side panels 34 can be releasably attached to the absorbent chassis 32 in the front waist region 22 of the training pant 20 as will be discussed hereinafter in more detail. Alternatively, the side panels 34 may be permanently bonded to the side edges 47 in the front waist region 22 and releasably attached to the side edges 36 in the back waist region 24 if it is desired that the fasteners be located towards the back of the wearer. Such a configuration may be desirable to prevent a wearer from unfastening the article prematurely.

Each of the side panels 34 can include one or more individual, distinct pieces of material. In particular embodiments, for example, each side panel 34 can include front and back side panel portions that are joined at a seam (see FIG. 4). Still alternatively, each individual side panel 34 can include a single piece of material which is folded over upon itself along an intermediate fold line (not shown).

The side panels 34 desirably comprise an elastic material capable of stretching in a direction parallel to the transverse axis 49 of the training pant 20. In particular embodiments, each side panel 34 may comprise an interior portion 78 disposed between the distal edge 68 and the center panel 35 of the back waist region 24. In the illustrated embodiment, the interior portion 78 is disposed between the distal edge 68 and the side edges 47 of the rectangular composite structure 33. The elastic material of the side panels 34 can be disposed in the interior portions 78 to render the side panels elastomeric in a direction parallel to the transverse axis 49. Most desirably, each side panel 34 is elastomeric from the waist end edge 72 to the leg end edge 70. More specifically, individual samples of side panel material, taken between the waist end edge 72 and the leg end edge 70 parallel to the transverse axis 49 and having a length from the attachment line 66 to the distal edge 68 and a width of 2 centimeters, are all elastomeric.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42.

The training pant 20 according to the present invention also includes a fastening system 80 for securing the training pant about the waist of the wearer (FIGS. 2 and 3). The illustrated fastening system 80 includes first and second fastening components 82 and 83 that are adapted to refastenably connect to first and second mating fastening components 84 and 85. In one embodiment, one surface of each of the first and second fastening components 82 and 83 comprises a plurality of engaging elements that project from that surface. The engaging elements of these fastening components 82 and 83 are adapted to repeatedly engage and disengage the engaging elements of the mating fastening components 84 and 85.

In one particular embodiment, the first and second fastening components 82 and 83 each comprise hook type fasteners and the first and second mating fastening components 84 and 85 each comprise complimentary loop type fasteners. In another particular embodiment, the first and second fastening components 82 and 83 each comprise loop type fasteners and the first and second mating fastening components 84 and 85 each comprise complimentary hook type fasteners. Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 and 83 or the mating fastening components 84 and 85 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

With reference to FIG. 3, the first and second fastening components 82 and 83 are desirably located on the inner surface 28 of the training pant 20 in the back waist region 24. The first and second fastening components 82 and 83 are desirably positioned along the distal edge 68 of the side panels 34. The first and second fastening components 82 and 83 can be adhered to the side panels 34 by any means known to those skilled in the art such as adhesive bonds, sonic bonds or thermal bonds.

With reference to FIG. 2, the first and second mating fastening components 84 and 85 can be located on the outer surface 30 of the training pant 20 in the front waist region 22. The first and second mating fastening components 84 and 85 are sized to receive the first and second fastening components 82 and 83 and are desirably positioned along the side edges 36 of the absorbent chassis 32, and in particular along the linear side edges 47 of the rectangular composite structure 33, abutting the front waist edge 38. In particular embodiments, the mating fastening components 84 and 85 have their inner side edges 86 disposed transversely outward from and closely adjacent to the side edges 76 of the absorbent batt 75. Moreover, the leg elastic members 58 are desirably axially aligned with the mating fastening components 84 and 85. The front terminal points 63 of the leg elastic members 58 are desirably located adjacent inner end edges 87 of the respective mating fastening components 84 and 85, and the back terminal points 65 of the leg elastic members are desirably located adjacent the longitudinally innermost parts of the side panels 34.

The first and second mating fastening components 84 and 85 can be adhered to the outer cover 40 by any means known to those skilled in the art such as adhesive bonds, sonic bonds or thermal bonds. In an alternative embodiment, the training pant 20 includes only a single mating fastening component disposed in the front waist region 22 for refastenably connecting to the first and second fastening components 82 and 83 (not shown). In a further alternative embodiment, the outer cover 40 and/or bodyside liner 42 functions as a mating fastening component in that it comprises a material that is releasably engageable with the first and second fastening components 82 and 83. In other alternative embodiments, the fastening components are located on the outer surface and the mating fastening components are located on the inner surface. The first and second mating fastening components 84 and 85 are desirably rectangular, although they may alternatively be square, round, oval, curved or otherwise nonrectangularly shaped.

When the fastening components and the mating fastening components 82-85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. Due to the composite structure 33 being rectangular and the side panels 34 being attached in the back waist region 24, the side edges 36 of the absorbent chassis 32 in the front waist region 22 and the crotch region 26 are aligned with one another and are parallel to the longitudinal axis 48, that is they form common linear edges.

When connected, the fastening components and the mating fastening components 82-85 form a refastenable seam 88 (FIG. 1). In particular embodiments, each of the fastening components and the mating fastening components 82-85 define a length dimension that is aligned generally parallel with the longitudinal axis 48 of the training pant 20 and a width dimension that is aligned generally parallel with the transverse axis 49 of the training pant. For a child of about 9 to abut 15 kilograms (20-35 lbs.), for example, the length dimension of the fastening components and mating fastening components is desirably from about 5 to about 13 centimeters, such as about 10 centimeters, and the width dimension is desirably from about 0.5 to about 3 centimeters, such as about 2 centimeters. The fastening components and the mating fastening components desirably have a length-to-width ratio of about 2 or greater, such as about 2 to about 25, and Particularly about 5 or greater, such as about 5 to about 8. Alternatively, the fastening components and refastenable seams may be curved or otherwise non-linear.

The refastenable seams 88 desirably extend substantially the entire distance between the waist opening 50 and the leg openings 52 when the fasteners 82-85 are engaged. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82 and 83 that are disposed on the side panels 34 can be formed to cover about 80 to 100 percent, and more particularly about 90 to about 98 percent, of the distance between the waist end edge 70 and the leg end edge 72 of the side panels.

The absorbent chassis 32 and the fastening system 80 together define a refastenable pant having a waist opening 50 and a pair of leg openings 52. When the fastening system is engaged, it can be appreciated that the refastenable pant includes a pair of refastenable seams 88 extending from the waist opening to each leg opening, a pair of elastomeric side panels 34 extending from the waist opening to each leg opening, an elastomeric front waistband 54 disposed in the front waist region and positioned between the pair of refastenable seams, an elastomeric back waistband 56 disposed in the back waist region and positioned between the pair of elastomeric side panels, and a pair of elastomeric leg members 58 which partially encircle each leg opening. Each elastomeric leg member 58 extends from adjacent a refastenable seam 88 in the front waist region 22 to adjacent an elastomeric side panel 34 in the back waist region 24.

Figure 4:
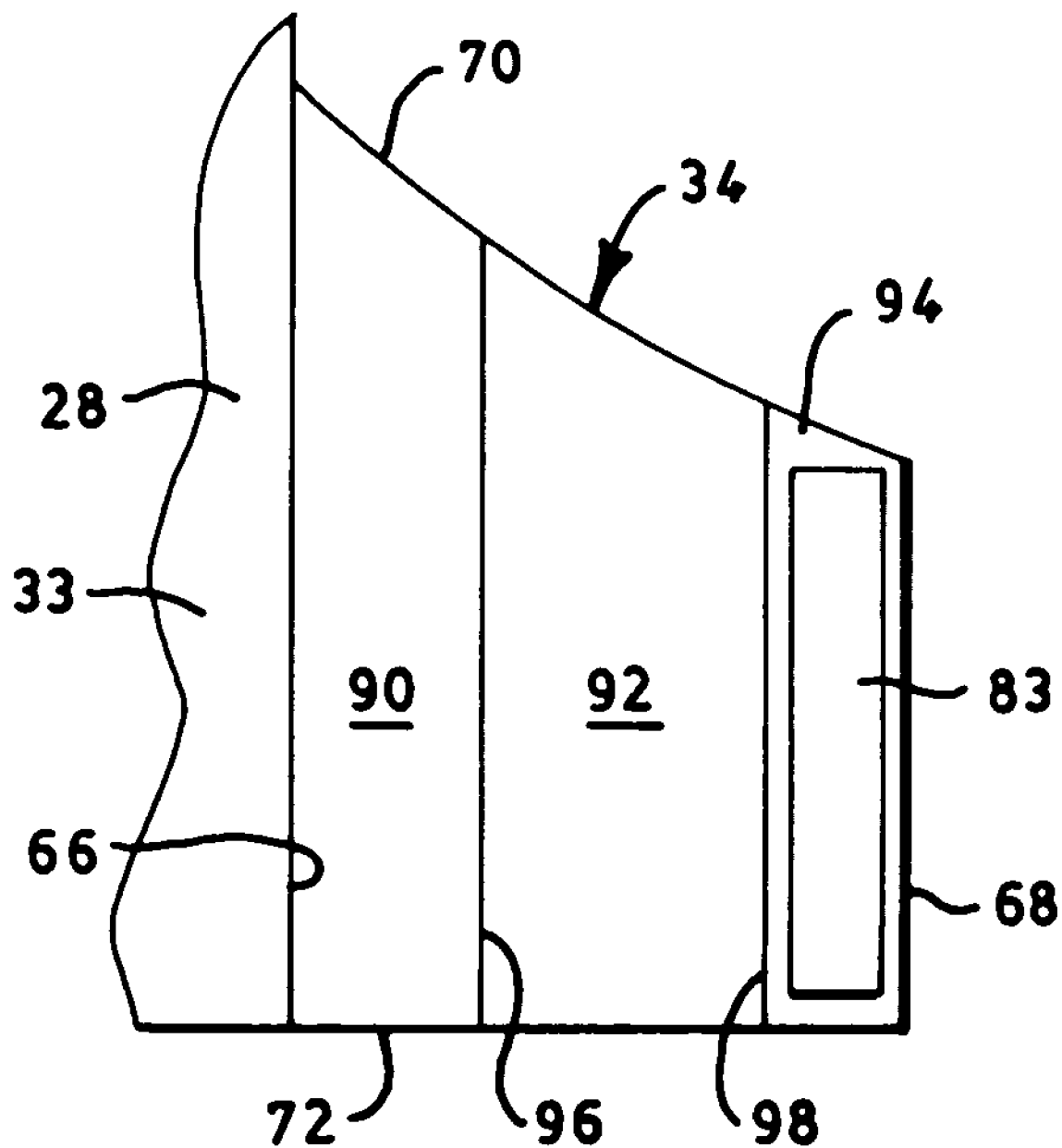
FIG. 4 illustrates a plan view of a side panel of an alternative disposable absorbent article incorporating the principles of the present invention, in an unfastened, stretched and laid flat condition and showing the surface of the article that faces the wearer when the article is worn.

A single side panel 34 of an alternative disposable absorbent article is shown in FIG. 4. The side panel 34 is bonded to a composite structure 33 at an attachment line 66. The side panel 34 includes a distal edge 68 transversely spaced from the attachment line 66 and a leg end edge 70 and a waist end edge 72 that extend from the composite structure to the distal edge. The side panel 34 illustrated in FIG. 4 includes a separate first member 90, second member 92, and third member 94 that are arranged in series from the attachment line 66 to the distal edge 68. The fastening component 83 is disposed on the third member 94 adjacent the distal edge 68.

The first member 90 and the second member 92 are desirably attached to one another at a manually tearable seam 96 that extends from the leg end edge 70 to the waist end edge 72. The tearable seam 96 is desirably formed of suitable means such as ultrasonic bonds that permit the side panel 34 to be torn easily at or along the tearable seam by the caregiver. The tearable seam 96 is desirably but not necessarily an outwardly directed fin seam. The second member 92 and the third member 94 are desirably attached to one another at a permanent seam 98 that extends from the leg end edge 70 to the waist end edge 72. The permanent seam 98 may be formed by adhesives, sonic or thermal bonds, or some combination thereof and is designed to resist tearing. In particular embodiments, the first and second members 90 and 92 comprise elastomeric materials and the third member 94 comprises a non-elastomeric material. Alternatively, the side panel may comprise two members, one or both of which may be elastomeric, that are bonded together at either a tearable seam or a permanent seam (not shown). A training pant incorporating the side panel 34 illustrated in FIG. 4 comprises a pair of refastenable seams and a pair of manually tearable seams 96.

Figure 5:
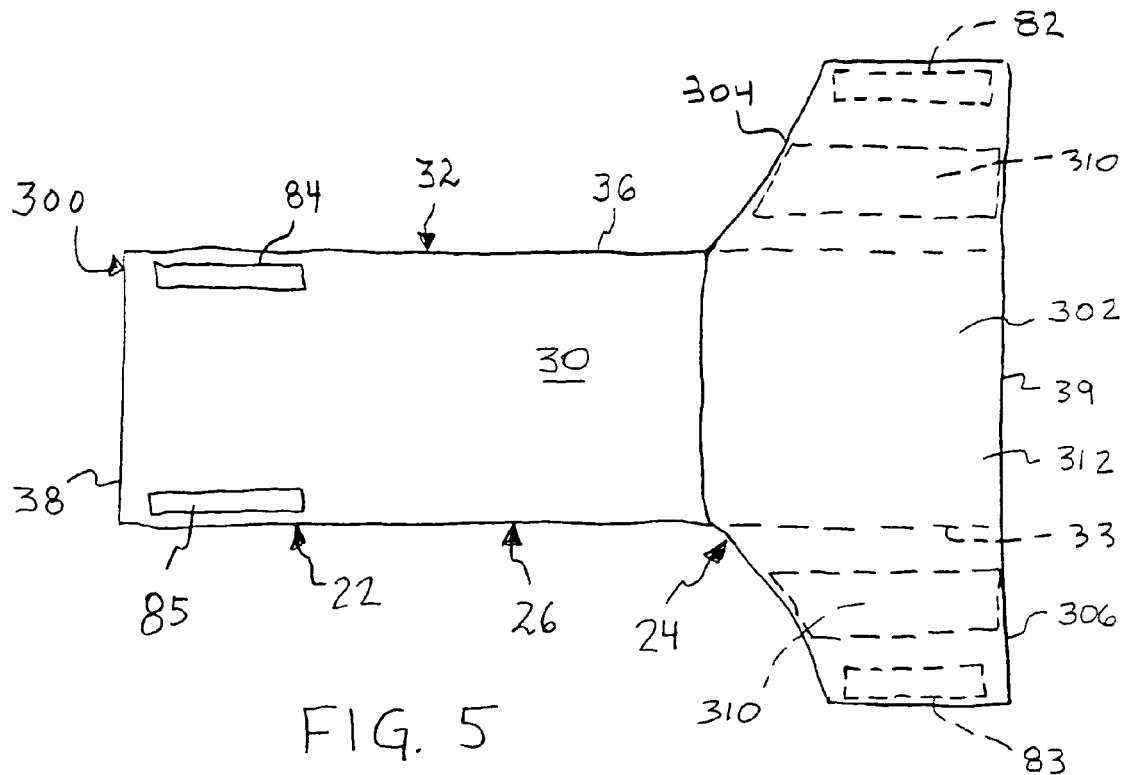
FIG. 5 illustrates a plan view of an alternative disposable absorbent article shown in an unfastened, stretched and laid flat condition, and showing the surface of the article that faces away from the wearer.

An alternative training pant 300 is illustrated in a stretched and laid flat condition in FIG. 5. The training pant 300 includes first and second mating fastening components 84 and 85 disposed in the front waist region 22 on the outer surface 30. The training pant 300 also includes a panel member 302 disposed in the back waist region 24. The panel member 302 desirably forms first and second side panels 304 and 306 that extend transversely outward from the composite structure 33 and the absorbent assembly 44 (FIG. 3) in the back waist region 24. First and second fastening components 82 and 84 of the training pant 300 are bonded to the inner surface 28 of the side panels 304 and 306.

Figure 6:
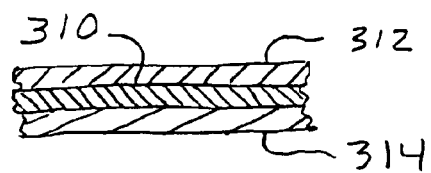
FIG. 6 illustrates an enlarged sectional view of a portion of an attachment panel of the absorbent article shown in FIG. 5.

The panel member 302 can comprise an integral portion of a component of the composite structure 33, such as the bodyside liner 42 or a layer of the outer cover 40; or comprise a separate element bonded to the composite structure; or comprise a plurality of layers, whether integral portions, separate elements, or a combination thereof. The panel member 302 and thus the side panels 304 and 305 can comprise either an elastic material or an inelastic material. With additional reference to FIG. 6, the panel member 302 in the illustrated embodiment comprises a plurality of elastomeric segments 310 disposed between an outer facing layer 312 and an inner facing layer 314.

The elastomeric segments 310 can be positioned and arranged so that both side panels 304 and 305 have elastic properties in a direction parallel to the transverse axis 49 of the training pant 300. The elastomeric segments 310 can comprise elastomeric films, webs, strands, fibers or the like, and can comprise elastic materials similar to those described in relation to other elastic components of the training pants 20 and 300. The facing layers 312 and 314 can comprise materials of the type described in relation to the bodyside liner 42, the side panels 34, or the like.

Figure 7:
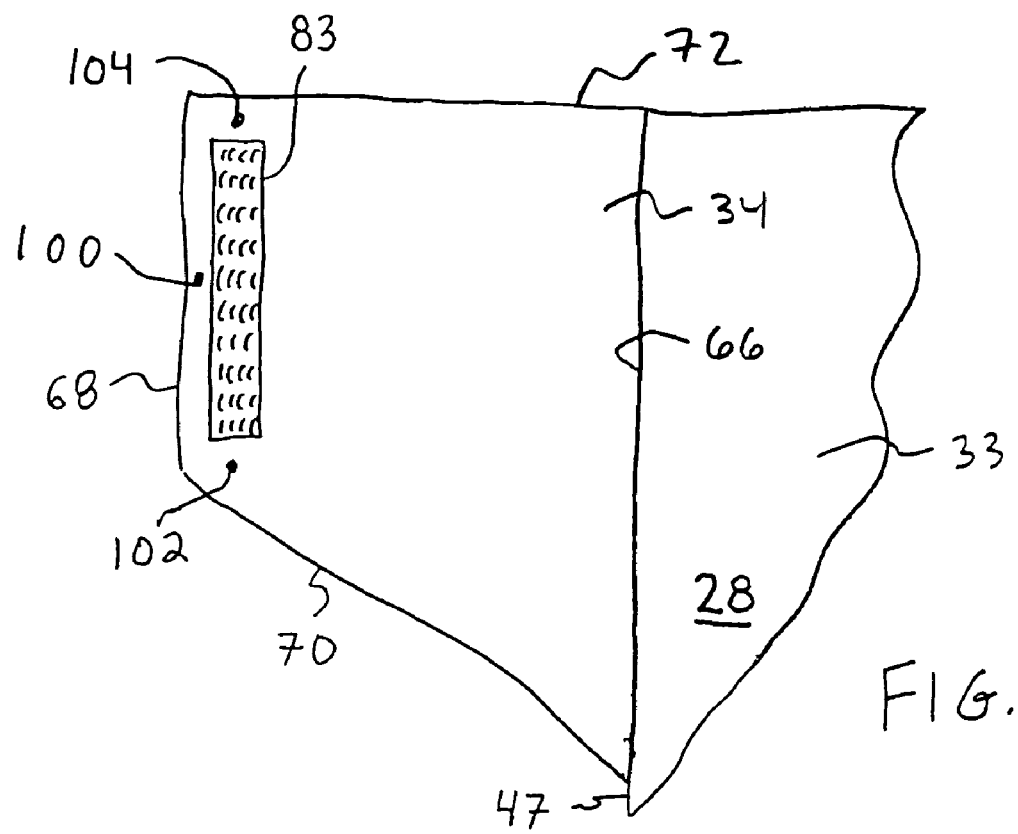
FIG. 7 illustrates an enlarged plan view of a back side panel of the type shown in FIG. 5.

An enlarged plan view of a back side panel 34 of the type shown in FIG. 1 is illustrated in FIG. 7. Only one side panel 34 is shown in FIG. 7, although it should be understood that other side panels can employ a similar construction. The side panel 34 can be bonded to and extend transversely beyond the linear side edge 47 of the composite structure 33 along attachment line 66. The side panel 34 defines a distal edge 68 that is spaced from the attachment line 66, a leg end edge 70 disposed toward the longitudinal center of the training pant 20, and a waist end edge 72 disposed toward a to longitudinal end of the training pant. Alternatively, the side panels can comprise an integral portion of a component of the composite structure 33, such as the bodyside liner or the outer cover.

In particular embodiments, the fastening component 83 is spaced inward from the distal edge 68 and the end edges 70 and 72 in order to protect the wearer from irritation that might be caused by contact with the fastening component. Specifically, the fastening component 83 can be spaced transversely inward from the distal edge 68 in the region of reference numeral 100. Also, the fastening component 83 can be spaced longitudinally inward from the leg end edge 70 in the region of reference numeral 102, and spaced longitudinally inward from the waist end edge 72 in the region of reference numeral 104.

The degree of spacing balances the fact that a smaller distance is harder for children and parents to remove but provides a more garment-like appearance, while a larger distance is easier for children and parents to remove but provides a loose and floppy appearance that is not garment-like. Thus, the fastening component 83 is desirably spaced transversely inward from the distal edge 68 by about 1 to about 15 millimeters, particularly about 1 to about 5 millimeters, such as about 2 millimeters. The fastening component 83 is desirably spaced longitudinally inward from the leg end edge 70 and from the waist end edge 72 by about 2 millimeters or more, particularly about 5 millimeters or more, such as from about 5 to about 15 millimeters.

Figure 8:
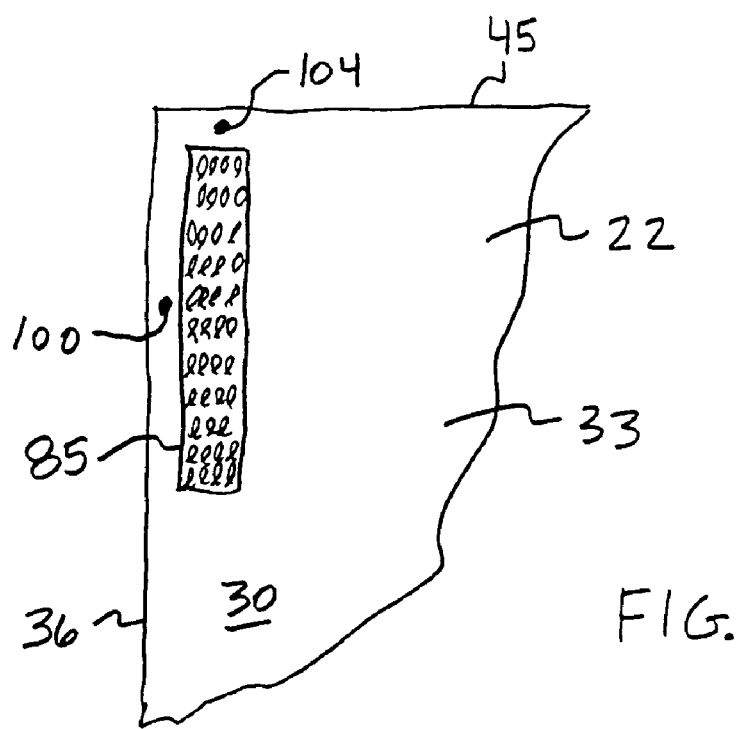
FIG. 8 illustrates an enlarged plan view of a front side panel of the type shown in FIG. 5.

FIG. 8 illustrates an enlarged plan view of a front waist region 22 including a mating fastening component 85. As with the embodiment illustrated in FIG. 7, the fastening component 85 can be spaced transversely inward from the side edge 36 in the region of reference numeral 100 and longitudinally spaced inward from the end edge 45 in the region of reference numeral 104. The preferred distances from the edges are the same as those specified above in relation to the embodiment of FIG. 7.

The training pants 20 and 300 may further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. patent application Ser. No. 09/100,574 titled "Disposable Absorbent Articles Having Passive Side Bonds And Adjustable Fastening Systems" filed Jun. 19, 1998 by Elsberg, which is incorporated herein by reference.

The methods of the different aspects of the present invention are directed at reliably and consistently providing the refastenable training pants 20 and 300 as described herein and representatively illustrated in the Figures. The various components of the training pant 20 are integrally assembled together employing various types of suitable attachment means, such as adhesive, sonic and thermal bonds or combinations thereof.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article, comprising:

an absorbent chassis comprising a bodyside liner, an outer cover bonded to the bodyside liner, and an absorbent assembly disposed between the bodyside liner and the outer cover, the absorbent chassis defining a longitudinal axis, a transverse axis, an overall length dimension, first and second waist edges parallel to the transverse axis, opposite side edges extending between the first and second waist edges, a first waist region contiguous with the first waist edge, a second waist region contiguous with the second waist edge, and a crotch region which extends between and interconnects the first and second waist regions, the side edges in the first waist region and crotch region being aligned with one another parallel to the longitudinal axis;

first and second side panels extending transversely outward from the absorbent assembly in the second waist region, the side panels having opposite edges and an average length dimension that is about 20 percent or greater of the overall length dimension;

leg elastic members longitudinally aligned along each side edge; and a fastening system for releasably securing the absorbent article in a pant-like configuration, the fastening system comprising first and second fastening components adapted to releasably engage first and second mating fastening components, each of the fastening components and the mating fastening components having a length dimension aligned generally parallel to the longitudinal axis, a width dimension, and a length-to-width ratio of about 5 or greater, the fastening components being disposed on the side panels and covering about 80 to 100 percent of the distance between the opposite edges of the side panels, the mating fastening components being disposed in the first waist region along the opposite side edges abutting the first waist edge, the leg elastic members being axially aligned with the mating fastening components.

2. The absorbent article of claim 1, wherein each leg elastic member has a front terminal point and a back terminal point, the front terminal points being located adjacent inner end edges of the respective mating fastening components.

3. The absorbent article of claim 2, wherein the front terminal points are located within about 2 centimeters of the mating fastening components.

4. The absorbent article of claim 2, wherein the back terminal points are located adjacent longitudinally innermost parts of the side panels.

5. The absorbent article of claim 4, wherein the back terminal points are located within about 2 centimeters of the longitudinally innermost parts of the side panels.

6. The absorbent article of claim 1, wherein each side panel is elastomeric from a waist end edge to a leg end edge.

7. The absorbent article of claim 1, wherein the absorbent assembly includes an absorbent batt having opposite side edges generally longitudinally oriented within the absorbent chassis, and the mating fastening components have inner side edges disposed transversely outward from and adjacent to the side edges of the absorbent batt.

8. An absorbent article, comprising:
a generally inelastic absorbent chassis comprising a bodyside liner, an outer cover bonded to the bodyside liner, and an absorbent assembly disposed between the bodyside liner and the outer cover, the absorbent chassis defining a longitudinal axis, a transverse axis, first and second waist edges parallel to the transverse axis, opposite side edges extending between the first and second waist edges, a first waist region contiguous with the first waist edge, a second waist region contiguous with the second waist edge, and a crotch region which extends between and interconnects the first and second waist regions;
first and second elastomeric side panels extending transversely outward from the absorbent assembly in the second waist region; and
a fastening system for releasably securing the absorbent article in a pant-like configuration, the fastening system comprising first and second fastening components adapted to releasably engage first and second mating fastening components, the fastening components being disposed on the elastomeric side panels and having a length dimension, a width dimension, and a length-to-width ratio of about 2 or greater, the mating fastening components being disposed on the generally inelastic absorbent chassis in the first waist region and positioned along the opposite side edges abutting the first waist edge, the mating fastening components having a length dimension, a width dimension, and a length-to-width ratio of about 2 or greater wherein each first and second fastening component has a length-to-width ratio of about 5 or greater.

9. The absorbent article of claim 8, further comprising leg elastic members longitudinally aligned along each side edge and axially aligned with the mating fastening components.

10. The absorbent article of claim 8, further comprising leg elastic members longitudinally aligned along each side edge, each leg elastic member having a front terminal point and a back terminal point, the front terminal points being located within about 2 centimeters of inner end edges of the respective mating fastening components.

11. The absorbent article of claim 10, wherein the back terminal points are located adjacent longitudinally innermost parts of the side panels.

12. The absorbent article of claim 8, wherein each side panel is elastomeric from a waist end edge to a leg end edge.

13. The absorbent article of claim 8, wherein the absorbent assembly includes an absorbent batt having opposite side edges generally longitudinally oriented within the absorbent chassis, and the mating fastening components have inner side edges disposed transversely outward from and adjacent to the side edges of the absorbent batt.

14. The absorbent article of claim 8, wherein the side edges in the first waist region and crotch region are aligned with one another and are parallel to the longitudinal axis.

15. The absorbent article of claim 8, wherein the mating fastening components have a length dimension aligned generally parallel to the longitudinal axis, a width dimension, and a length-to-width ratio of about 5 or greater.

16. An absorbent article, comprising a generally inelastic absorbent chassis and a fastening system for releasably attaching a front waist region of the absorbent chassis to a back waist region of the absorbent chassis to define a refastenable pant having a waist opening and a pair of leg openings, the refastenable pant comprising:
a pair of refastenable seams extending from the waist opening to each leg opening;
a pair of elastomeric side panels extending from the waist opening to each leg opening;
an elastomeric front waistband disposed in the front waist region and positioned between the pair of refastenable seams, at least part of the front waistband being transversely axially aligned with the pair of refastenable seams;
an elastomeric back waistband disposed in the back waist region and positioned between the pair of elastomeric side panels; and
a pair of elastomeric leg members which partially encircle each leg opening, each elastomeric leg member extending from adjacent a refastenable seam in the front waist region to adjacent an elastomeric side panel in the back waist region.

17. The absorbent article of claim 7, wherein the mating fastening components abut the respective opposite side edges of the absorbent chassis.

18. The absorbent article of claim 13, wherein the mating fastening components abut the respective opposite side edges of the generally inelastic absorbent chassis.

19. The absorbent article of claim 16, wherein the fastening system comprises first and second fastening components adapted to releasably engage first and second mating fastening components, the fastening components being disposed on the elastomeric side panels and having a length dimension, a width dimension, and a length-to-width ratio of about 2 or greater, the mating fastening components being disposed on the generally inelastic absorbent chassis in the front waist region and positioned along opposite side edges of the generally inelastic absorbent chassis and abutting a front waist edge of the front waist region, the mating fastening components having a length dimension, a width dimension, and a length-to-width ratio of about 2 or greater.

* * * * *